US00PP19393P2

(12) United States Plant Patent
Korlipara

(10) Patent No.: US PP19,393 P2
(45) Date of Patent: Oct. 28, 2008

(54) ***COREOPSIS* PLANT NAMED 'TROPICAL LEMONADE'**

(50) Latin Name: ***Coreopsis* hybrid**
Varietal Denomination: Tropical Lemonade

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 11/827,158

(22) Filed: Jul. 10, 2007

(51) Int. Cl.
*A01H 5/00* (2006.01)

(52) U.S. Cl. ..... Plt./417
(58) Field of Classification Search ..... Plt./417
See application file for complete search history.

(56) References Cited

U.S. PATENT DOCUMENTS

PP15,455 P3 * 12/2004 Faria ..... Plt./417

OTHER PUBLICATIONS

UPOV ROM GTITM Computer Database, GTI Jouve Retrieval Software, May 2007, Citation for 'Tropical Lemonade'/'Sunshine Scarlet'(Trade Name).*
U.S. Appl. No. 11/343,831 to Korlipara filed Jan. 30, 2006.
U.S. Appl. No. 11/343,832 to Korlipara filed Jan. 30, 2006.
U.S. Appl. No. 11/344,356 to Korlipara filed Jan. 30, 2006.

* cited by examiner

*Primary Examiner*—Wendy C. Haas
(74) *Attorney, Agent, or Firm*—Klarquist Sparkman, LLP

(57) ABSTRACT

A new and distinct *Coreopsis* plant named 'Tropical Lemonade' characterized by golden-yellow foliage, red-orange, daisy-type flowers, dwarf mounding habit, and very free flowering.

1 Drawing Sheet

Figure 1:
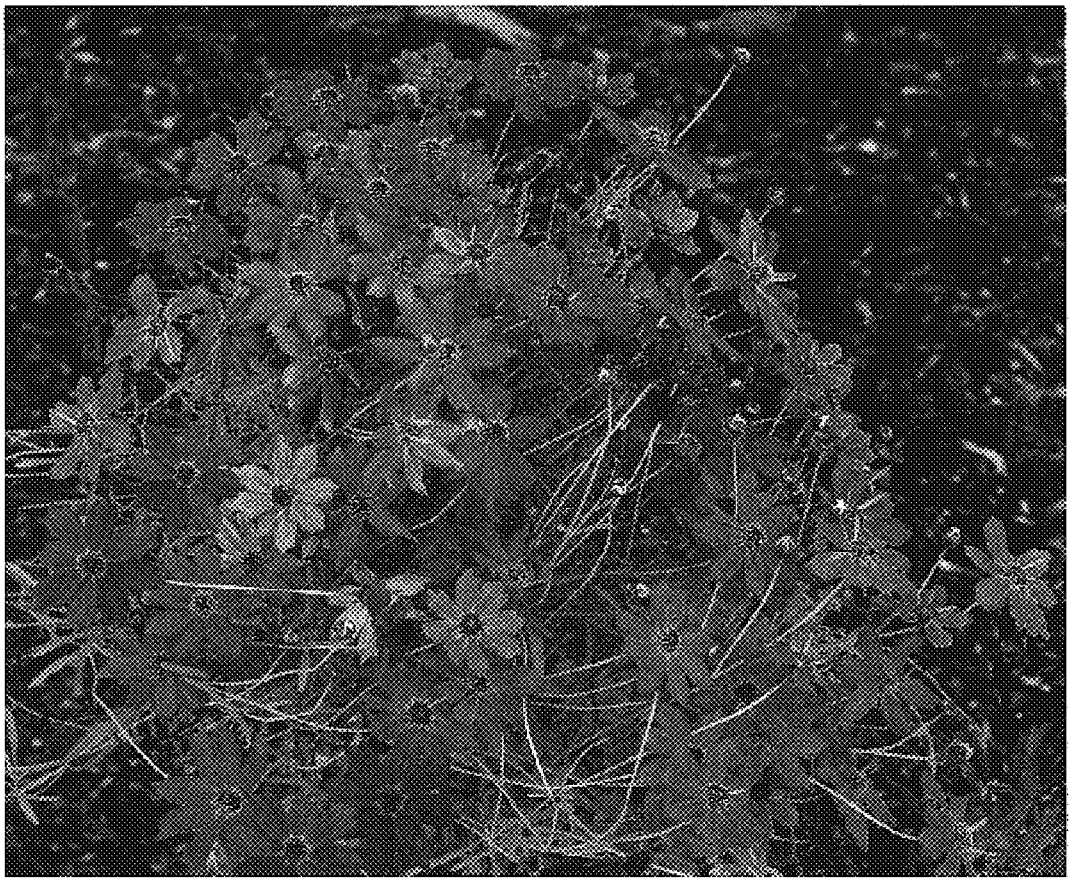

Botanical designation: *Coreopsis* hybrid.
Variety denomination: 'Tropical Lemonade'.

BACKGROUND OF THE INVENTION

The present invention relates to a new and distinct plant of *Coreopsis* and given the cultivar name 'Tropical Lemonade'. *Coreopsis* is in the family Asteraceae. This new cultivar originated as a branch mutation from offspring located at Terra Nova Nurseries in Canby, Oreg. and reproduced in tissue culture where further selections were made. This selection was made for its red-orange flowers.

SUMMARY OF THE INVENTION

The following traits have been repeatedly observed and are determined to be the unique characteristics of 'Tropical Lemonade'. These characteristics in combination distinguish 'Tropical Lemonade' as a new and distinct cultivar:

1. Golden-yellow foliage.
2. Red-orange, daisy-type flowers.
3. Dwarf mounding habit.
4. Very free flowering.

This new cultivar has been reproduced only by asexual propagation (cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE PHOTOGRAPH

FIG. 1 shows a one-year-old *Coreopsis* 'Tropical Lemonade' growing in the ground in the garden in August in Canby, Oreg.

DETAILED PLANT DESCRIPTION

The following is a detailed description of the new *Coreopsis* cultivar based on observations of a one-year-old specimen grown in the ground in full sun under typical outdoor conditions in the garden in August in Canby, Oreg. Canby is Zone 8 on the USDA Hardiness map. Temperatures ranging from a high of 95 degrees F. in August to 32 degrees F. in January. Normal rainfall in Canby is 42.8 inches per year. The color descriptions are all based on The Royal Horticultural Society Colour Chart.

Plant:
- *Type.*—Herbaceous perennial.
- *Hardiness.*—USDA Zones 9–10.
- *Size.*—40 cm wide and 25 cm tall to top of flowers.
- *Form.*—Low mound with freely branching stems.
- *Vigor.*—Good.
- *Roots.*—Fibrous, freely branching, fine and White 155A in color, roots develop easily from cuttings.

Stem:
- *Type.*—Ascending.
- *Size.*—20 cm tall and 1 to 2 mm wide.
- *Internode length.*—12 to 30 mm.
- *Surface.*—Glabrous.
- *Color.*—Yellow Green 146C.

Leaf:
- *Type.*—Simple.
- *Shape.*—Linear.
- *Arrangement.*—Opposite.

*Length.*—25 to 40 mm, sessile.

*Width.*—1 to 2 mm.

*Margins.*—entire.

*Apex.*—Acute.

*Base.*—Attenuate.

*Surface texture.*—Glabrous, soft and smooth to the touch.

*Venation.*—Pinnate.

*Color.*—Top side Yellow 10A with a green main vein Yellow Green 146C to Yellow Green 146A where shaded, bottom side same as top side.

Inflorescence:

*Type.*—Long stalked terminal heads.

*Peduncle.*—7 cm tall and 1 mm wide, glabrous, Yellow 10A to Yellow Green 146C where shaded.

*Size.*—2.5 to 3.5 cm wide and 8 mm deep.

*Ray florets.*—8 in number, no stamen or pistil, obovate with the tip three lobed with lobes obtuse and the central lobe the longest, base attenuate, margin entire, grows to 17 mm long, 8 mm wide; glabrous, soft and velvety to the touch; color topside Greyed Purple 184A overlaying Yellow Orange 22B with younger flowers darker than older flowers, bottom side Greyed Orange 177C with edges Greyed Purple 184A lightening with maturity.

*Disc florets.*—All together form a small rounded "cone", 4 mm wide and becoming 3 mm deep with maturity, Brown 200B when in bud, opening to Orange 24A with a dark background, Greyed Purple 187A; about 55 in number, each 5 mm long and 1 mm wide, tubular, 4 lobed, Greyed Purple 187A at the apex to Orange 24A in middle and Yellow Orange 20B near base; pistil one in number, 6 mm long, Orange 24A overall, extruding, 2-branched stigma, ovary 1.5 mm long, style 4 mm long; stamen 4 in number, filaments 3 mm long, extruding, Black 202A, pollen Yellow 12C.

*Bloom period.*—June through September in Canby, Oreg.

*Fragrance.*—Light, daisy like.

Seed: None produced.

*Fertility.*—Infertile.

Disease and pests. *Coreopsis* are susceptible to mildew and fungal spots. None of these have been observed on plants grown under commercial conditions in Canby, Oreg.

COMPARISONS TO SIMILAR *COREOPSIS*

Compared to *Coreopsis* 'Limerock Ruby' (U.S. Plant Pat. No. 15,455), this new cultivar has the same flower size. It is different in its yellow foliage, dwarf habit and red purple flower color.

Compared to the other *Coreopsis* in the "Lemonade series" (including 'Pink Lemonade' U.S. Plant Pat. No. 18,265, 'Cherry Lemonade' U.S. Plant Pat. No. 18,334 and 'Strawberry Lemonade' U.S. Plant Pat. No. 18,299), 'Tropical Lemonade' has a different flower color.

I claim:

1. A new and distinct *Coreopsis* plant named 'Tropical Lemonade' as herein illustrated and described.

* * * * *